United States Patent
Brandenburger et al.

(10) Patent No.: US 8,162,915 B2
(45) Date of Patent: Apr. 24, 2012

(54) CONNECTOR FOR PACKINGS CONTAINING MEDICAL LIQUIDS, AND CORRESPONDING PACKING FOR MEDICAL LIQUIDS

(75) Inventors: Torsten Brandenburger, Niddatal (DE); Klaus Heilmann, St. Wendel (DE); Bernd Knierbein, Neu-Anspach (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 122 days.

(21) Appl. No.: 10/550,477

(22) PCT Filed: Jan. 22, 2004

(86) PCT No.: PCT/EP2004/000487
§ 371 (c)(1),
(2), (4) Date: Aug. 22, 2006

(87) PCT Pub. No.: WO2004/084793
PCT Pub. Date: Oct. 7, 2004

(65) Prior Publication Data
US 2008/0009783 A1    Jan. 10, 2008

(30) Foreign Application Priority Data
Mar. 27, 2003  (DE) .................................. 103 13 760

(51) Int. Cl.
*A61B 19/00* (2006.01)
*A61M 5/32* (2006.01)
(52) U.S. Cl. ....................................... 604/415; 604/403
(58) Field of Classification Search .................. 604/262, 604/403, 408, 409, 411, 415; 215/230, 232, 215/247, 250, 258, 316, DIG. 3; 206/219, 206/222; 137/68.11, 68.19, 68.29, 68.3, 67; 141/314, 329, 330, 363
See application file for complete search history.

(56) References Cited

U.S. PATENT DOCUMENTS

| | | | | | |
|---|---|---|---|---|---|
| 3,917,120 A | * | 11/1975 | Larenz et al. | .................. | 222/129 |
| 3,986,506 A | * | 10/1976 | Garber et al. | .................. | 604/406 |
| 3,986,507 A | * | 10/1976 | Watt | .................. | 604/408 |
| 3,994,412 A | * | 11/1976 | Difiglio | .................. | 220/266 |
| 4,150,673 A | * | 4/1979 | Watt | .................. | 604/408 |
| 4,228,835 A | * | 10/1980 | Robinson et al. | .................. | 604/408 |

(Continued)

OTHER PUBLICATIONS

Online encyclopedia article "Polypropylene" accessed Dec. 18, 2008. http://en.wikipedia.org/wiki/Polypropylene.*

(Continued)

*Primary Examiner* — Tatyana Zalukaeva
*Assistant Examiner* — Philip R Wiest
(74) *Attorney, Agent, or Firm* — Mayer Brown LLP

(57) ABSTRACT

A connector for packings containing medical liquids, particularly infusion, transfusion or enteral bags, comprises a connecting part (1) for accommodating a spike for drawing out the liquid and comprises a closure part (3) that closes the passage (2) inside the connecting part (1). The connecting part (1) has an elastically deformable pinching off part (4) provided in the form of a tubular section with a non-circular cross-section. A base part (5), which widens on both sides is adjoined to said pinching off part (4) and can be integrated in the packing. During manufacturing, the packing is filled with liquid via the connecting part. After filling, the pinching off part is pressed together whereby preventing liquid from escaping. Afterwards, the closure part is placed onto the connecting part. The manufacturing of the packing is simplified by virtue of the fact that an additional tube for connecting the connector and packing is rendered unnecessary.

20 Claims, 5 Drawing Sheets

U.S. PATENT DOCUMENTS

Figure 1:
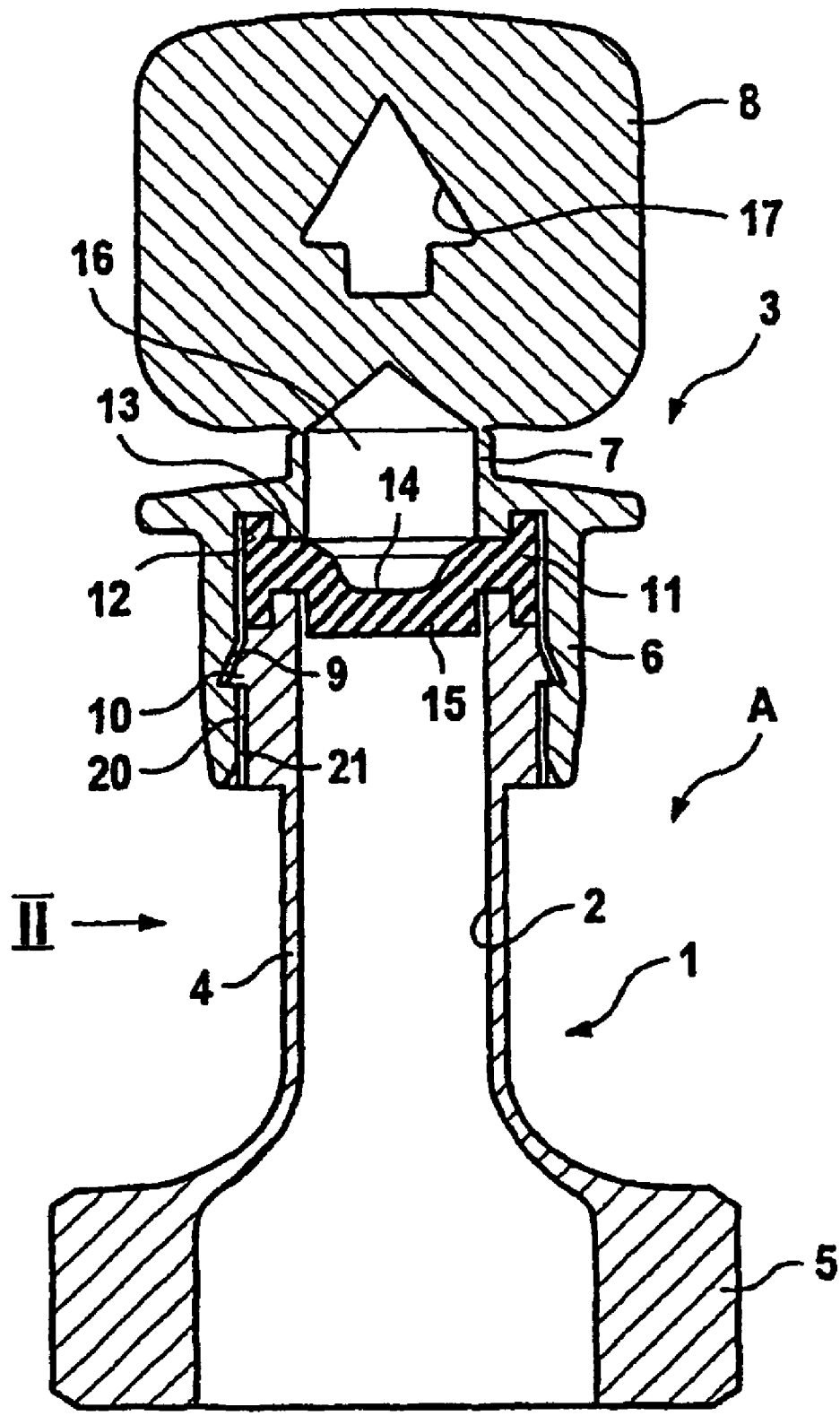

| | | | |
|---|---|---|---|
| 4,295,495 A * | 10/1981 | Rosemeier et al. | 138/89 |
| 4,415,393 A * | 11/1983 | Grimes | 156/244.13 |
| 4,502,616 A * | 3/1985 | Meierhoefer | 222/215 |
| 4,632,267 A * | 12/1986 | Fowles et al. | 215/253 |
| 4,641,362 A * | 2/1987 | Muller | 383/115 |
| 4,836,397 A * | 6/1989 | Fowles | 220/214 |
| 4,854,737 A * | 8/1989 | Steer et al. | 383/127 |
| 4,857,190 A * | 8/1989 | Wada et al. | 210/232 |
| 4,892,222 A * | 1/1990 | Schmidt et al. | 215/247 |
| 4,903,855 A * | 2/1990 | Ducay et al. | 220/802 |
| 4,944,736 A * | 7/1990 | Holtz | 604/403 |
| 4,951,822 A * | 8/1990 | Fontana et al. | 206/530 |
| 4,975,186 A * | 12/1990 | Wada et al. | 210/232 |
| 4,979,630 A * | 12/1990 | Rose et al. | 215/47 |
| 5,030,211 A * | 7/1991 | Zakroczymski | 604/262 |
| 5,228,782 A * | 7/1993 | Imer | 383/200 |
| 5,368,586 A * | 11/1994 | Van Der Heiden et al. | 604/403 |
| 5,380,314 A * | 1/1995 | Herweck et al. | 604/403 |
| 5,409,125 A * | 4/1995 | Kimber et al. | 215/48 |
| D358,466 S * | 5/1995 | Harris et al. | D24/115 |
| 5,429,256 A * | 7/1995 | Kestenbaum | 215/247 |
| 5,494,170 A * | 2/1996 | Burns | 215/247 |
| 6,116,449 A * | 9/2000 | Chiesi et al. | 220/23.4 |
| 6,234,333 B1 * | 5/2001 | Federighi et al. | 215/48 |
| 6,280,431 B1 * | 8/2001 | Domkowski et al. | 604/411 |
| 6,330,959 B1 * | 12/2001 | Dark | 222/153.1 |
| D456,507 S * | 4/2002 | LeMarr et al. | D24/115 |
| 6,364,143 B1 * | 4/2002 | Knierbein | 215/247 |
| 6,378,714 B1 * | 4/2002 | Jansen et al. | 215/249 |
| 6,485,479 B1 * | 11/2002 | Knierbein | 604/411 |
| 6,709,424 B1 * | 3/2004 | Knierbein | 604/411 |
| 6,723,076 B1 * | 4/2004 | Strobel | 604/262 |
| 6,752,264 B2 * | 6/2004 | Versluys | 206/219 |
| 7,594,578 B2 * | 9/2009 | Smith et al. | 206/438 |
| 7,879,015 B2 * | 2/2011 | Villefrance et al. | 604/332 |
| 2003/0105448 A1 * | 6/2003 | Shiraishi et al. | 604/415 |

OTHER PUBLICATIONS

Online article "Elastic Plastic Moving From Lab to Industry" accessed Dec. 18, 2008. http://www.scienceblog.com/community/older/1997/B/199701265.html.*

* cited by examiner

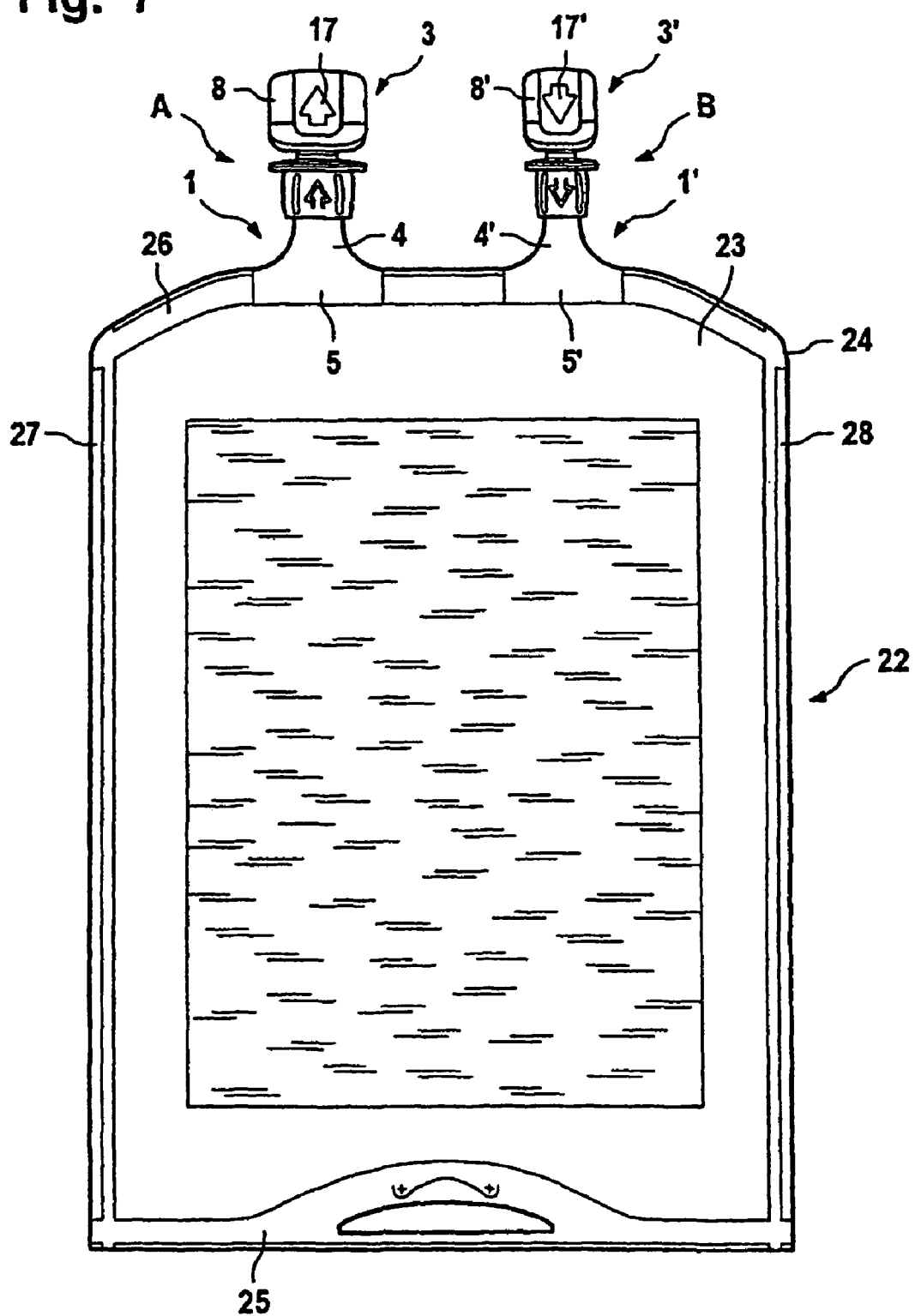

CONNECTOR FOR PACKINGS CONTAINING MEDICAL LIQUIDS, AND CORRESPONDING PACKING FOR MEDICAL LIQUIDS

The invention relates to a connector for packings, particularly infusion, transfusion or enteral bags, which contain medical liquids, particularly infusion solutions or enteral or parenteral feed solutions. The invention additionally relates to a packing for medical liquids, particularly an infusion, transfusion or enteral bag, having at least one such connector.

DE-A-197 28 775 describes an infusion bag with an injection part and a withdrawal part. The injection part is intended for delivering a medicament by means of an injection syringe, whereas the withdrawal part is used for withdrawing the solution by means of a spike. Injection part and withdrawal part have a tubular connecting part which is sealed by a protective cap designed as a part that can be broken off.

Injection part and withdrawal part are connected to the infusion bag or transfusion bag by means of a tube section. To fill the bag with feed solution, a filling rod at a filling station is inserted into the tube section protruding from the bag, and the bag is filled with feed solution. The tube section is then pinched off, and the bag is delivered to a connector attachment station. There, the injection or withdrawal part is fitted onto the tube section, and the tube section and the injection or withdrawal part are welded to one another. A disadvantage is that, when producing the bag, an additional tube section is needed. A further disadvantage is that filling of the bag and attachment of the injection or withdrawal part take place at different stations.

Therefore, it is an object of the invention to make available a connector for packings containing medical liquids, particularly infusion, transfusion or enteral bags, which simplifies the production of the bag. This object is achieved by the features set forth in patent claim 1.

A further object of the invention is to provide a packing for medical liquids, particularly an infusion, transfusion or enteral bag, which is easy to produce. This object is achieved by the features set forth in patent claim 10.

The connector according to the invention for packings containing medical liquids, particularly infusion, transfusion or enteral bags, makes it possible to fill the packing and also to apply the connector at one station. It is an advantage that an additional tube section for joining the connector and the packing is not required. This dispenses with the cutting of the tube section and with the complicated positioning.

The connector according to the invention comprises a connecting part with a passage for accommodating a spike for withdrawal of the liquid, and a closure part which can be fitted onto the connecting part and closes the passage in the connecting part. It is of crucial importance that the packing can be filled through the connecting part. Only after the packing has been filled can the closure part be fitted onto the connecting part.

The connecting part has an elastically deformable pinching-off part designed as a tubular portion with a noncircular cross section. After the packing has been filled, the connecting part can be pinched off with a suitable clamping device such that, when the closure part is fitted, there is no danger of liquid escaping from the packing.

The elastically deformable pinching-off part also allows the packing to be filled in a horizontal position, which is of advantage especially in the case of large-volume bags. Since the cross section of the pinching-off part is noncircular, the pinching-off part can be clamped with relatively slight forces, irrespective of the material used. It is important that the pinching-off part is elastically deformable so that it assumes its original shape again after the pinching. This makes it possible to avoid an undesired reduction of the cross section of the passage in the connecting part.

In addition, the pinching-off part makes it possible to close the connector with a clip or the like during use in a hospital.

The pinching-off part is adjoined by a base part which widens to both sides and which can be integrated in the packing, preferably welded to the bag.

To reduce the required assembly work, the closure part and the connecting part of the connector according to the invention are preferably secured with a snap fit. The snap-fit connection permits attachment of various closure parts which can be of different designs depending on the particular application (infusions, transfusions or enteral nutrition). However, both parts can be welded or adhesively bonded to one another. In addition to the shape fit, an additional weld connection is also possible.

In a further preferred embodiment, a self-sealing membrane arranged between the connecting part and the closure part prevents escape of liquid from the packing after withdrawal of the spike.

The membrane is fitted between the connecting part and the closure part only after the packing has been filled. The membrane is preferably held clamped with elastic deformation between the connecting part and the closure part. Consequently, the connector can be assembled in a simple manner by pressing of the individual parts. Since the parts are held clamped together, there is no danger of damaging the membrane during welding.

A further preferred embodiment involves a closure part with a cap-shaped bottom part which is adjoined, via an annular break zone, by a top part that can be broken off. This top part at the same time forms a tamper-evident closure.

The top part that can be broken off is preferably designed as a flat grip piece which can be gripped with the thumb and index finger.

To identify the direction of flow, i.e. whether the part in question is an injection part or a withdrawal part, the cap-shaped bottom part and/or the flat grip piece of the closure part is preferably identified by an arrow indicating the direction of flow. The arrow is preferably designed as a recess and/or as a raised structure.

The base part that can be integrated in the packing is preferably designed in the shape of a boat which can be welded to the film sheets more simply than a tubular body. Such a boat has by now become widely used in connectors.

The packing according to the invention for medical liquids, particularly an infusion, transfusion or enteral bag, has at least one connector, preferably two connectors, of which one is designed as an injection part and the other as a withdrawal part.

Figure 2:
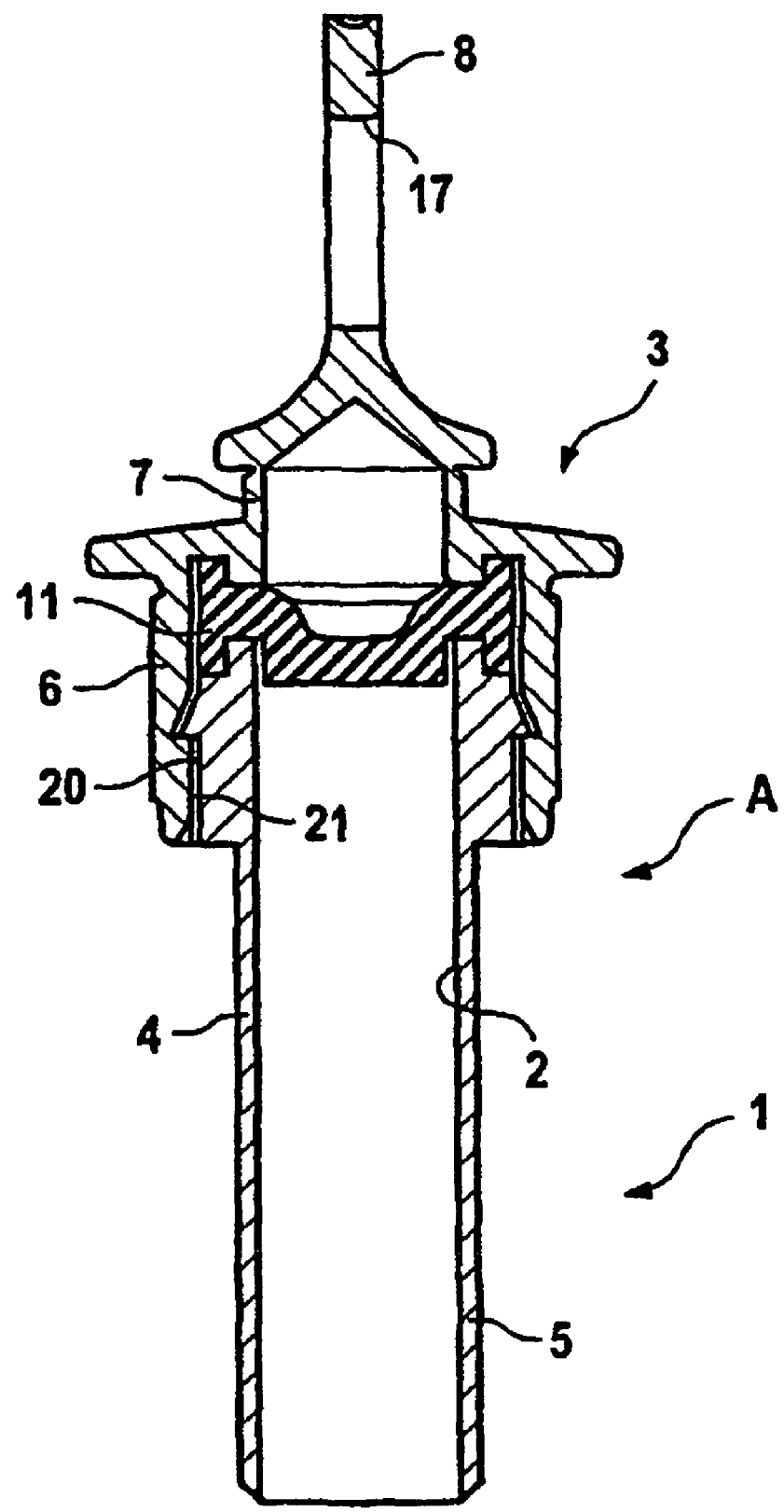
Figure 3:
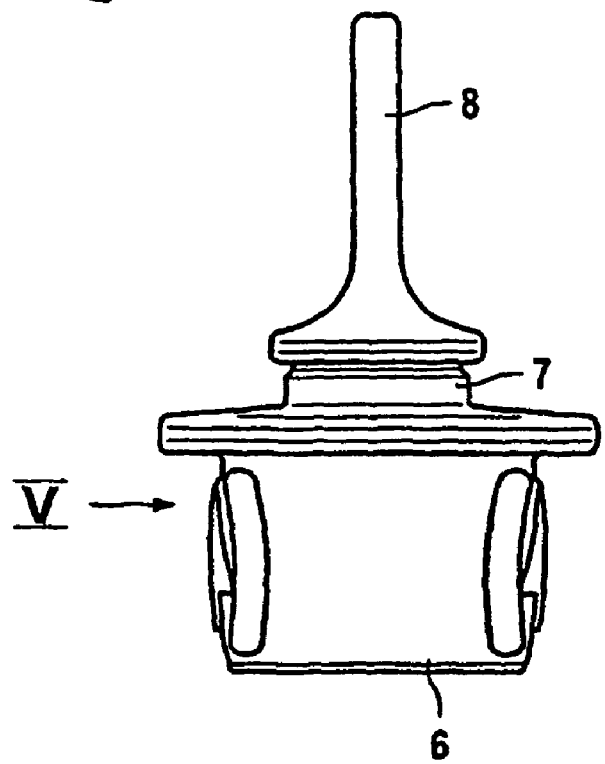
Figure 4:
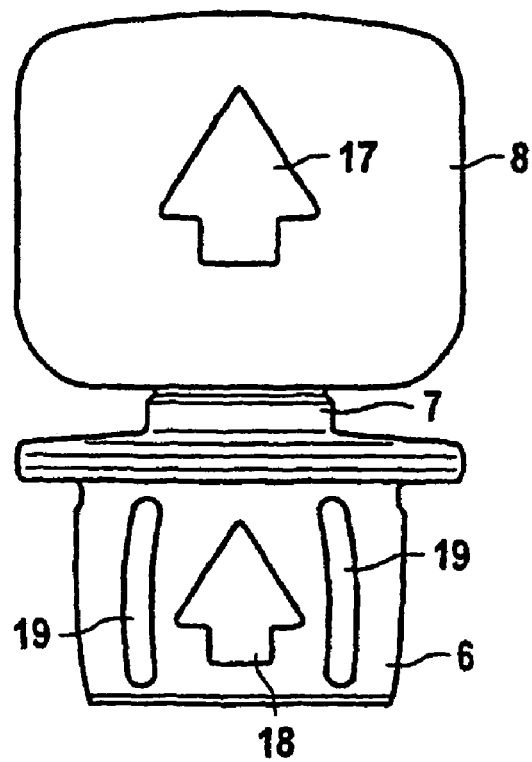
Figure 5A:
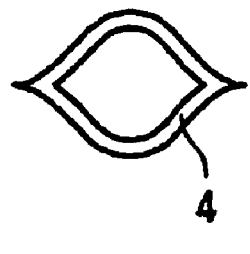
Figure 6A:
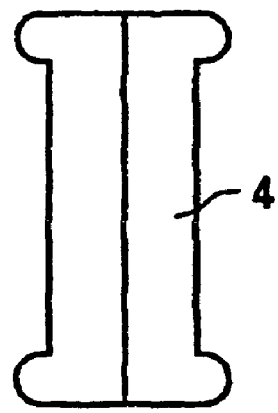

An illustrative embodiment of the invention is explained in more detail below with reference to the drawings, in which:

FIG. 1 shows, in cross section, a connector designed as a withdrawal part for a bag containing nutrient solution, FIG. 2 shows the connector from FIG. 1 from the direction of the arrow II, FIG. 3 shows the closure part of the connector from FIG. 1 in a side view, FIG. 4 shows a view of the closure part from FIG. 3 from the direction of the arrow V, FIGS. 5a+5b show two different cross-sectional shapes of the elastically deformable pinching-off part, and FIGS. 6a+6b show two alternative embodiments of the pinching-off part, and FIG. 7 shows a film bag for parenteral feed solution, with an injection part and a withdrawal part.

The connector A designed as a withdrawal part, for example for a bag containing parenteral feed solution, comprises a connecting part 1 with a passage 2 for accommodating a spike (not shown) for withdrawal of the liquid. A closure part 3 is fitted onto the connecting part 1 and closes the passage 2 in the connecting part 1. Connecting part and closure part are injection-molded components made of polypropylene.

Figure 5B:
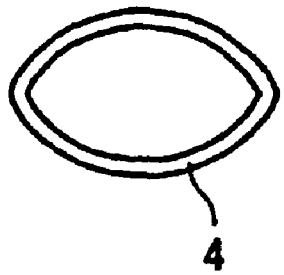

The connecting part 1 has an elastically deformable pinching-off part 4 designed with a noncircular cross section. FIGS. 5*a* and 5*b* show alternative cross-sectional shapes of the pinching-off part 4. A common feature of all the cross-sectional shapes is that the extent of the pinching-off part is different in two mutually perpendicular directions. This ensures that the pinching-off part can be pressed together with relatively slight forces. It is imperative that the pinching-off part does not break when it is pressed together.

Figure 6B:
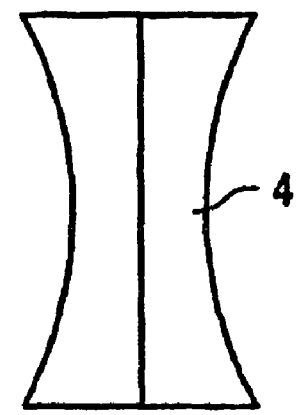

The pinching-off part can be designed in different ways in the longitudinal direction. For example, a constant reduction of the cross section in the longitudinal direction is possible. The pinching-off part can also be provided with a constriction. These alternatives are shown in FIGS. 6*a* and 6*b*.

The pinching-off part 4 is adjoined by a base part 5 which widens to both sides and which is designed in the shape of a boat with side pieces running out to a point. The upper and lower faces of the boat can simply be welded to the insides of the upper and lower film sheets of the bag.

The closure part 3 has a cap-shaped bottom part 6 which is adjoined, via an annular break zone 7, by a top part 8 that can be broken off. The cap-shaped bottom part 6 of the closure part 3 is secured by being snapped onto a cylindrical shoulder of the closure part 1. The inside wall of the bottom part 6 has a peripheral groove 9 into which a peripheral projection 10 on the outside wall of the cylindrical shoulder of the closure part 1 snaps when both parts 1 and 3 are pressed together.

A self-sealing membrane 11, also referred to as a septum, is held clamped with elastic deformation between the closure part 3 and the connecting part 1. The self-sealing membrane 11 has an outer portion 12 which is clamped between the cylindrical shoulder of the connecting piece 1 and the bottom part 6 of the closure part 3. The outer portion 12 is adjoined by an upper annular portion 13 which merges into a lower plate-shaped portion 15, thus forming a trough-like depression 14 on the top face of the membrane. At the center, the plate-shaped portion 15 is pre-slit in a cross shape or star shape, in such a way that the elastic material, although weakened, is not cut through.

The grip piece 8 of the closure part 3 closes the upper opening 16 for withdrawal of the feed solution and is designed as a flat body which can be easily gripped and twisted off with the thumb and index finger. At the center of the grip piece, there is an arrow-shaped recess 17. On two opposite sides of the bottom part 6 of the closure part 3 there is also an arrow 18 which is designed, however, as a raised structure and is arranged between two borders 19 forming a recessed grip (FIGS. 3 and 4).

To secure the closure part 3 and the connecting part 1 against twisting, the inside face of the cap-shaped bottom part 6 and the outside face of the cylindrical neck of the withdrawal part 1 are provided with spline-shaped inner and outer teeth 20, 21 respectively (FIGS. 1 and 2). The spline-shaped teeth arrangement means that the parts can be oriented exactly with respect to one another when being joined.

FIG. 7 shows a film bag 22 which is filled with a feed solution for parenteral nutrition and which comprises the connector A for withdrawal of the nutrient solution and a further connector B for injecting a solution into the infusion bag. The connector A is an injection part having the same structure as the withdrawal part. It again has a connecting part 1' and a closure part 3'. The opposite direction of flow is indicated by the arrow 17'. In this way, the withdrawal part and the injection part can be easily distinguished from one another.

The film bag 22 is made up of two film sheets 23, 24 which are welded together at the bottom and top edges 25, 26 and along the lengthwise edges 27, 28. At the upper edge of the bag, the boat-shaped base parts 5, 5' of the connectors A, B are welded in between the two film sheets 23, 24.

During production, the bag is filled via a filling rod which is inserted into the connecting part 1, 1' of one of the two connectors before the closure part 3, 3' is fitted onto the connecting part. The pinching-off part 4, 4' is then pinched by a suitable pinching device, which for example can comprise two mutually displaceable press elements, so that liquid cannot escape. The closure part 3 is then pressed onto the connecting part 1 so that both parts are secured with a snap fit. The connector A is closed in this way. To withdraw the nutrient solution, the break-off part 8 of the closure part 3 is broken off by turning it or breaking it so that the self-sealing membrane 11 is exposed. The spike of a known transfer system is now inserted into the opening 16 of the connecting part 1, as a result of which the pre-slit membrane 11 is pierced. The trough-like depression 14 of the membrane 11 serves as a guide for the spike. The spike is sealed off by the annular portion 13 of the membrane. By virtue of the special design of the membrane, the spike is held securely in the connecting part 1.

The parenteral nutrient solution can then be withdrawn. When the spike is drawn back out again, the membrane safely seals off the connecting part even in the event of a relatively high internal pressure. Moreover, the particular design of the membrane means that the mechanical strength of the connecting part is increased.

The injection part B is used to inject an active substance into the solution. For this purpose, after removal of the part 8' that can be broken off, the membrane is pierced again by an injection needle of a syringe. After withdrawal of the needle, the injection part again provides a seal. Enteral nutrition bags, by contrast, usually do not have an injection part, only a withdrawal part.

What is claimed is:

1. A connector for packings containing medical liquids, particularly infusion, transfusion or enteral bags, comprising:
   a connecting part that is an injection-molded component with a passage to accommodate a rod or a spike for filling or withdrawal of liquid, wherein the connecting part comprises,
      an elastically deformable pinching-off part, which re-assumes its original shape again after being pinched by a pinching device, and is designed as a tubular portion with a noncircular axial cross section that is different in two mutually perpendicular directions, and
      a base part that merges into the pinching-off part, wherein the base part widens to both sides and can be integrated in the packing, and wherein the pinching-off part comprises the same polymer as the base part; and
   a closure part which can be fitted onto the connecting part and closes the passage in the connecting part.

2. The connector as claimed in claim 1, characterized in that the closure part and the connecting part are secured with a snap fit.

3. The connector as claimed in claim 1 or 2, characterized in that a self-sealing membrane is arranged between the connecting part and the closure part and can be pierced by the spike for withdrawal of the liquid.

4. The connector as claimed in claim 3, characterized in that the self-sealing membrane is held clamped with elastic deformation between the connecting part and the closure part.

5. The connector as claimed in claim 1, characterized in that the closure part has a cap-shaped bottom part which is adjoined, via an annular break zone, by a top part that can be broken off.

6. The connector as claimed in claim 5, characterized in that the top part that can be broken off is designed as a flat grip piece.

7. The connector as claimed in claim 6, characterized in that the cap-shaped bottom part and/or the flat grip piece is identified by an arrow indicating the direction of flow.

8. The connector as claimed in claim 7, characterized in that the arrow is designed as a recess and/or as a raised structure.

9. The connector as claimed in claim 1, characterized in that the base part is designed in the shape of a boat.

10. A packing for medical liquids, particularly an infusion, transfusion or enteral bag, having at least one connector as claimed in claim 1.

11. A connector for packings containing medical liquids, comprising:
    a connecting part that is an injection-molded component with a passage to accommodate a rod or a spike for filling or withdrawal of liquid, wherein the connecting part comprises,
        an elastically deformable pinching-off part, which re-assumes its original shape again after being pinched by a pinching device, and is designed as a tubular portion with a noncircular axial cross section that is different in two mutually perpendicular directions, and
        a base part that merges into the pinching-off part, wherein the base part widens to both sides and can be integrated in the packing, and wherein the pinching-off part comprises the same polymer as the base part; and
    a closure part which can be fitted onto the connecting part and closes the passage in the connecting part.

12. The connector as claimed in claim 11, wherein the closure part and the connecting part are secured with a snap fit.

13. The connector as claimed in claim 11 or 12, wherein a self-sealing membrane is arranged between the connecting part and the closure part and can be pierced by the spike for withdrawal of the liquid.

14. The connector as claimed in claim 13, wherein the self-sealing membrane is held clamped with elastic deformation between the connecting part and the closure part.

15. The connector as claimed in claim 11, wherein the closure part has a cap-shaped bottom part which is adjoined, via an annular break zone, by a top part that can be broken off.

16. The connector as claimed in claim 15, wherein the top part that can be broken off is designed as a flat grip piece.

17. The connector as claimed in claim 16, wherein the cap-shaped bottom part and/or the flat grip piece is identified by an arrow indicating the direction of flow.

18. The connector as claimed in claim 17, wherein the arrow is designed as a recess and/or as a raised structure.

19. The connector as claimed in claim 11, wherein the base part is designed in the shape of a boat.

20. A packing for medical liquids having at least one connector as claimed in claim 11.

\* \* \* \* \*